(12) United States Patent
Lowe, Jr. et al.

(10) Patent No.: US 9,160,063 B2
(45) Date of Patent: Oct. 13, 2015

(54) WEARABLE DEVICE ASSEMBLY HAVING SOLDER MASK

(71) Applicant: Nike, Inc., Beaverton, OR (US)

(72) Inventors: Edward Stephen Lowe, Jr., Seattle, WA (US); Kate Richmond, Seattle, WA (US); Martine Stillman, Seattle, WA (US); Marco Micheletti, Seattle, WA (US)

(73) Assignee: Nike, Inc., Beaverton, OR (US)

( * ) Notice: Subject to any disclaimer, the term of this patent is extended or adjusted under 35 U.S.C. 154(b) by 111 days.

(21) Appl. No.: 13/745,361

(22) Filed: Jan. 18, 2013

(65) Prior Publication Data

US 2013/0188322 A1    Jul. 25, 2013

Related U.S. Application Data

(60) Provisional application No. 61/588,632, filed on Jan. 19, 2012.

(51) Int. Cl.
  *H05K 1/00* (2006.01)
  *H01Q 1/27* (2006.01)
  *G08C 19/16* (2006.01)
  (Continued)

(52) U.S. Cl.
  CPC ............ *H01Q 1/273* (2013.01); *A61B 5/0022* (2013.01); *A61B 5/02055* (2013.01); *A61B 5/11* (2013.01); *A61B 5/681* (2013.01); *A63B 24/0062* (2013.01); *G08C 19/16* (2013.01); *H04Q 9/00* (2013.01); *H05K 1/0281* (2013.01); *H05K 1/189* (2013.01); *H05K 7/06* (2013.01); *A63B 2220/40* (2013.01); *A63B 2220/836* (2013.01); *A63B 2225/50* (2013.01); *H04Q 2209/30* (2013.01); *H04Q 2209/43* (2013.01); *H04Q 2209/823* (2013.01); *H05K 2201/10098* (2013.01); *H05K 2201/10151* (2013.01)

(58) Field of Classification Search
  USPC .................................... 361/749, 761; 700/91
  See application file for complete search history.

(56) References Cited

U.S. PATENT DOCUMENTS 6,366,250 B1   4/2002   McConnell
6,513,532 B2   2/2003   Mault et al.
(Continued)

FOREIGN PATENT DOCUMENTS

DE   102010000778 A1   7/2011
GB       2280065 A    1/1995
(Continued)

OTHER PUBLICATIONS

PCT/US2013/022196 Written Opinion mailed Apr. 9, 2013, PCT European Patent Office.
(Continued)

*Primary Examiner* — Andargie M Aychillhum
(74) *Attorney, Agent, or Firm* — Banner & Witcoff, Ltd.

(57) ABSTRACT

A wrist-worn device monitors movements of a user. A curvilinear body of the wrist-worn device includes a plurality of flex areas, and an internal spine member of the wrist-worn device extends through the curvilinear body. A flexible circuit member is wrapped around and connected to the spine member. The flexible circuit member interconnects a controller and one or more sensors of a sensor assembly within the body. A solder mask applied to the flexible circuit member includes a curvilinear edge that distributes stress caused by flexing of the flexible circuit member.

19 Claims, 8 Drawing Sheets

(51) Int. Cl.

| | | |
|---|---|---|
| *H05K 7/06* | (2006.01) | |
| *A63B 24/00* | (2006.01) | |
| *H05K 1/02* | (2006.01) | |
| *H05K 1/18* | (2006.01) | |
| *A61B 5/00* | (2006.01) | |
| *A61B 5/0205* | (2006.01) | |
| *A61B 5/11* | (2006.01) | |
| *H04Q 9/00* | (2006.01) | |

(56) References Cited

U.S. PATENT DOCUMENTS

| | | |
|---|---|---|
| 2005/0012194 A1 | 1/2005 | Jaeck |
| 2005/0111306 A1 | 5/2005 | Saaski et al. |
| 2007/0021269 A1 | 1/2007 | Shum |
| 2009/0284937 A1 | 11/2009 | Rytky |
| 2012/0035508 A1 | 2/2012 | Van Leer |
| 2012/0253485 A1* | 10/2012 | Weast et al. .................... 700/91 |

FOREIGN PATENT DOCUMENTS

| | | |
|---|---|---|
| JP | 3088404 A | 4/1991 |
| JP | 9036630 A | 2/1997 |
| WO | 20100126821 A1 | 11/2010 |

OTHER PUBLICATIONS

PCT/US2013/022196 International Search Report mailed Apr. 9, 2013, PCT European Patent Office.

Mar. 25, 2013(WO)—ISR—App. No. PCT/US2013/022232.

Mar. 25, 2013 (WO)—Written Opinion—App. No. PCT/US2013/022232.

* cited by examiner

WEARABLE DEVICE ASSEMBLY HAVING SOLDER MASK

CROSS-REFERENCE TO RELATED APPLICATION

This application claims priority to U.S. Provisional Patent Application No. 61/588,632 filed on Jan. 19, 2012 and titled, "Wearable Device Assembly Having Flexible Circuit Member," which is herein incorporated by reference in its entirety.

TECHNICAL FIELD

Aspects of the invention generally relate to solder masks for electronic circuits and particularly relate to solder masks for flexible electronic circuits.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

A wrist-worn device that monitors movements of a user is provided. A curvilinear body of the wrist-worn device includes a plurality of flex areas, and an internal spine member of the wrist-worn device extends through the curvilinear body. A flexible circuit member is wrapped around and connected to the spine member. The flexible circuit member interconnects a controller and one or more sensors of a sensor assembly within the body. A solder mask applied to the flexible circuit member includes a curvilinear edge that distributes stress caused by flexing of the flexible circuit member.

The curvilinear edge may define solder mask peaks and valleys between the sides of the flexible circuit member. The solder mask peaks may exhibit a peak width and peak height, and the solder mask valleys may exhibit a valley width and valley depth. The number of solder mask peaks may match the number of solder mask valleys, peak width may match valley width, and peak height may match valley depth. The solder mask peaks and solder mask valleys may substantially also conform to a portion of a circle.

A solder mask for a flexible circuit member of a wrist-worn device that monitors movements of a user is also provided in accordance with the principles set forth above. The solder mask includes a curvilinear solder mask edge that distributes stress caused by flexing of the flexible circuit member. In some example embodiments, the curvilinear solder mask edge may be positioned proximate to a USB connector of the wrist-worn device.

BRIEF DESCRIPTION OF THE DRAWINGS

The present disclosure is illustrated by way of example and not limited in the accompanying figures in which like reference numerals indicate similar elements and in which.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

1. EXAMPLE PERSONAL TRAINING SYSTEM

1.1. Illustrative Computing Devices

Figure 1:
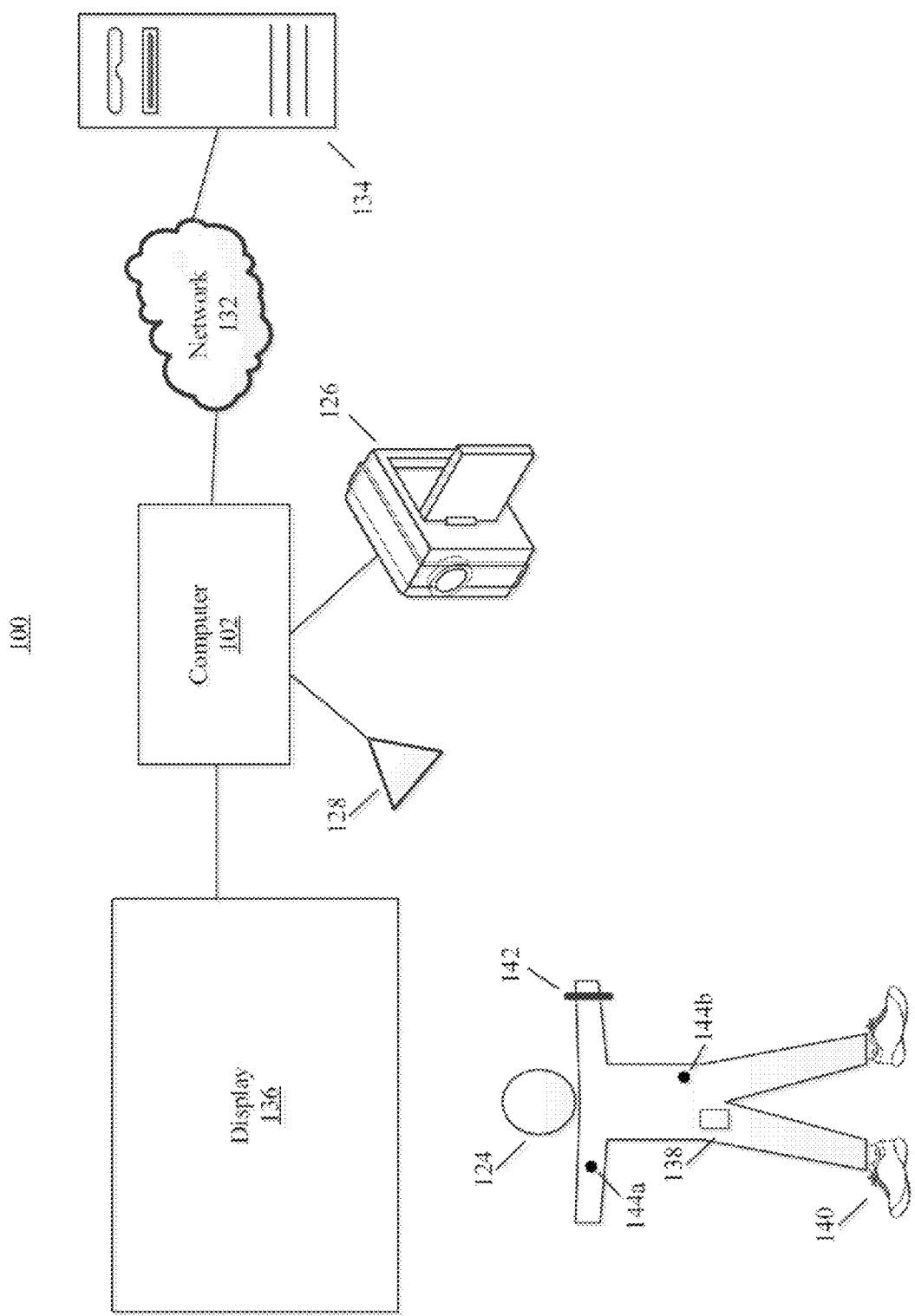
FIG. 1 is an example of an implementation of a system for providing personal training.

FIG. 1 illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® PlayStation, and/or a Nintendo® Wii gaming consoles. Those skilled in the art will appreciate that these are merely example consoles for descriptive purposes and this disclosure is not limited to any console or device.

Figure 2:
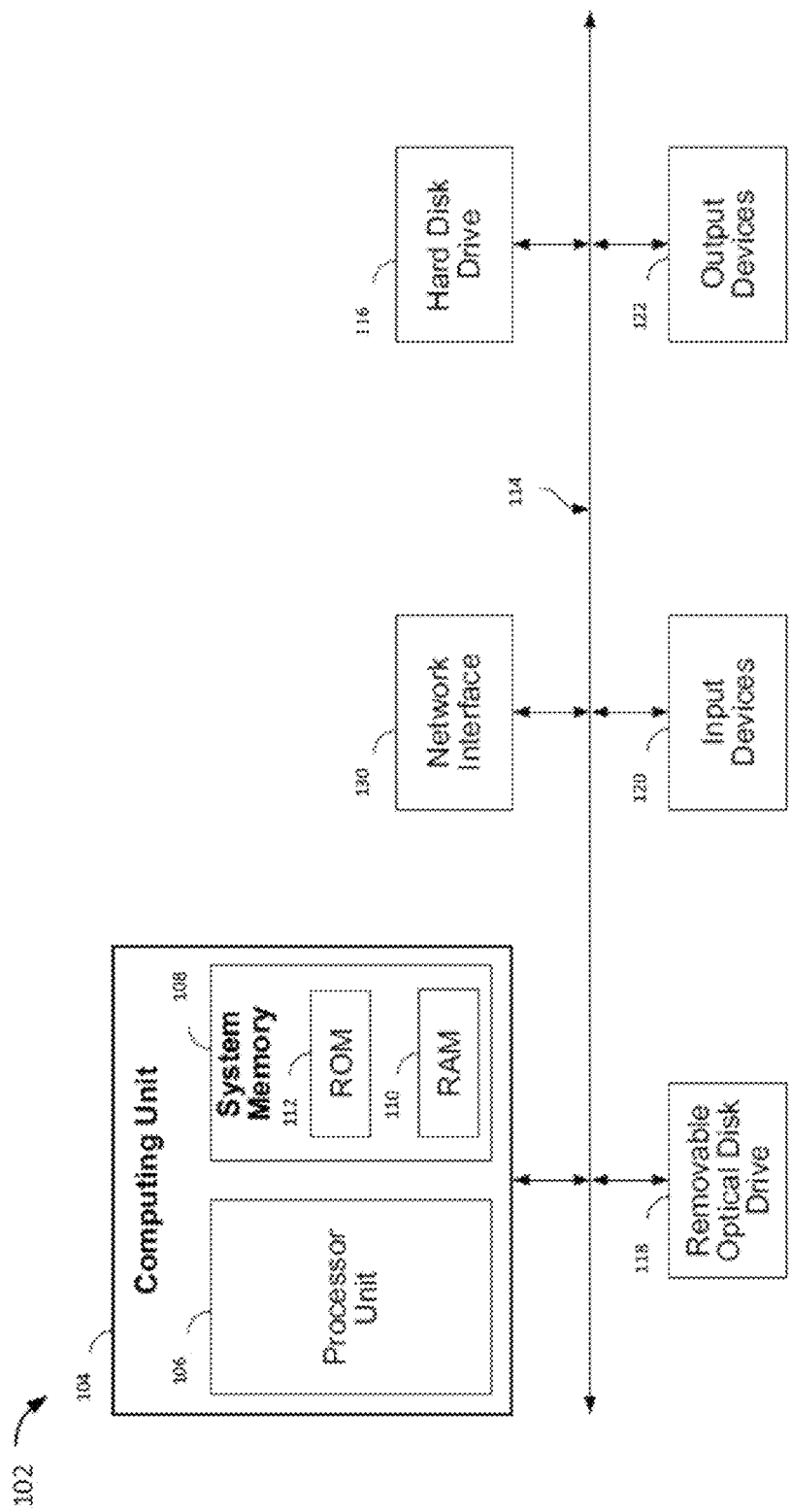
FIG. 2 is an example of an implementation of a computing device for providing personal training.

Turning briefly to FIG. 2, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1.

Looking again to FIG. 1, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

1.2. Illustrative Network

Computer 102, computing unit 104, and/or any other electronic devices may be directly or indirectly connected to one or more network interfaces, such as example interface 130 (shown in FIG. 2) for communicating with a network, such as network 132. In the example of FIG. 2, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

1.3. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1.3.1 Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may take place via computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 2 may be included in the server 134, other computers, apparatuses, etc.

1.3.2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

Figure 3:
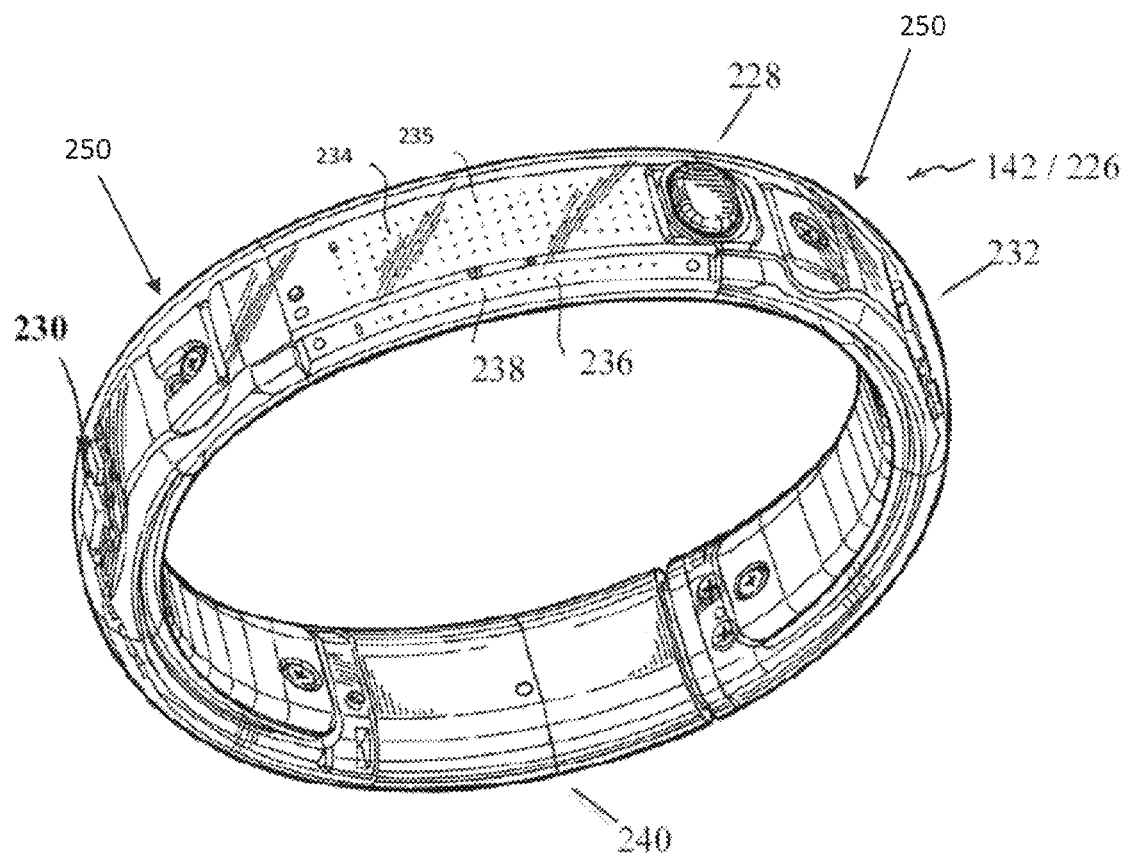
FIG. 3 is an example of an implementation of a wrist-worn sensor assembly device that monitors movements of a user.

As shown in FIG. 3, an example of an implementation of a wrist-worn sensory assembly device 226 is shown ("wrist-worn device" or "device"). The device 226 (which may resemble or be sensory device 142 shown in FIG. 1) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 3, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 2. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

It will be understood that the device 226 will undergo some flexing as the device is positioned around the wrist of a user 124 or removed from the wrist of the user 124. When the fastening mechanism 240 is unlatched and the device 226 pulled open, the device will flex at various flex areas 250 to allow the wrist to be received by the device as the device wraps around the wrist of the user 124. The device 226 flexes in a similar fashion when the fastening mechanism 240 is unlatched and the device pulled open to remove the device from the wrist of the user 124. In the example device 226 of FIG. 3, the device includes two flex areas 250 located near what may be described as the "shoulders" of the device.

In certain embodiments, device 226 may comprise a sensor assembly (not shown in FIG. 3). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and energy expenditure such as calories, heart rate, sweat detection, effort, oxygen consumed, and/or oxygen kinetics. Such parameters may also be expressed in terms of activity points or currency earned by the user based on the activity of the user.

2. ENERGY EXPENDITURE POINT CALCULATIONS

Figure 4:
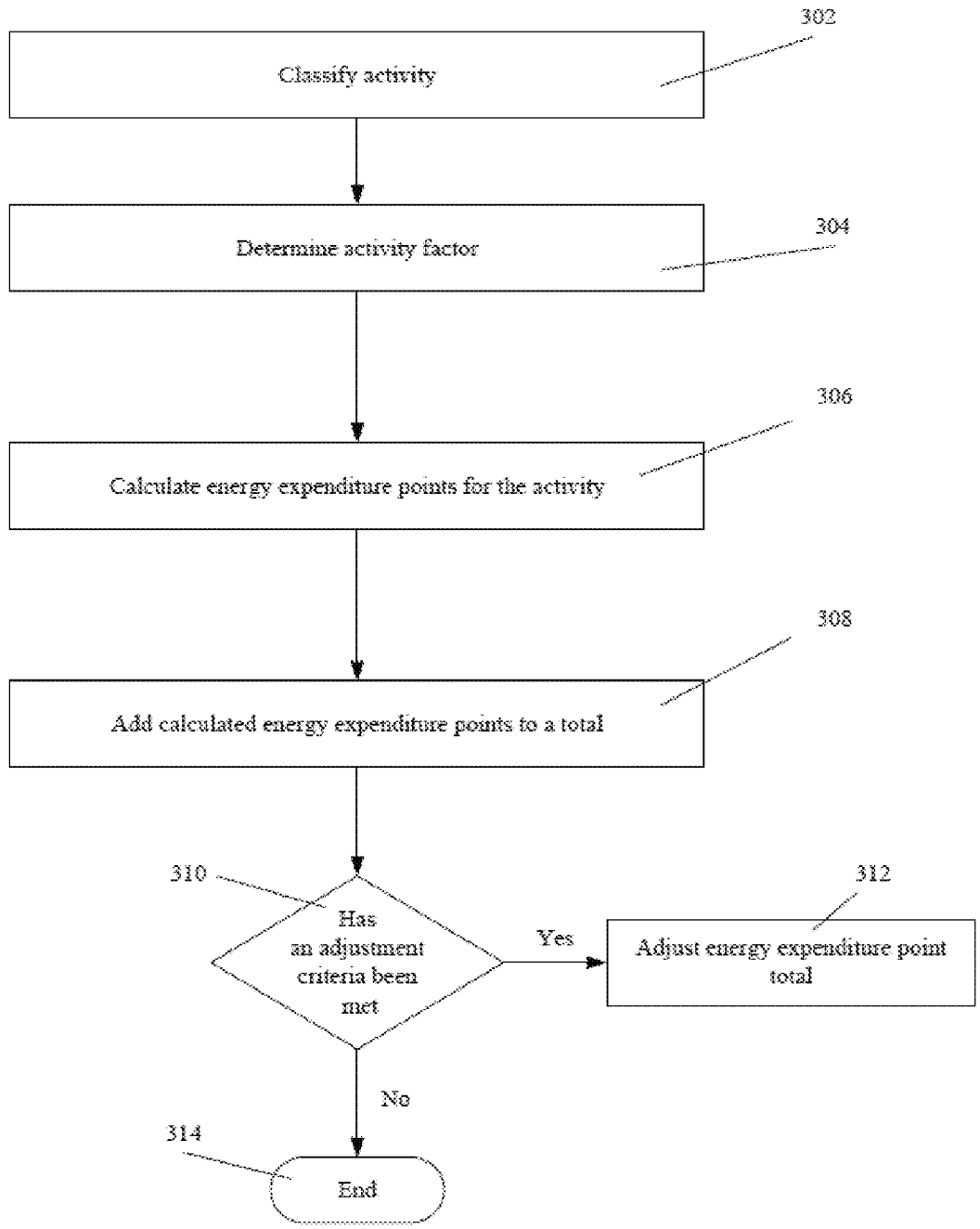
FIG. 4 is a flowchart of example method steps for calculating energy expenditure

FIG. 4 is a flow chart of example method steps for calculating energy expenditure values, such as points, in accordance with an embodiment of the invention. Certain embodiments may classify physical motions of a user. For example, at illustrative step 302, one or more activities may be classified. System 100 may process data received from one or more of the sensors described above to attempt to classify a user's activity. For example, system 100 may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may be created from data obtained from one or more of a plurality of different sensors. For example, a first group of sensors (e.g. sensors 126 and 138) may be utilized in the formation or refinement of a first activity template; however, a second group of sensors (e.g., sensors 128 and 140) may be utilized in the formation or refinement of a second activity template. In yet further embodiments, a third group of sensors, such as sensors 128 and 140 (and/or other sensors), may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example step 302 may include comparing a signal, multiple signals or a combination of signals to one or more templates.

In some embodiments, a best match approach may be implemented in which every activity is attempted to be classified. In other embodiments, if a signal, multiple signals or combination of signals does not sufficiently match a template, the activity may remain unclassified.

After at least one of user's 124 activity is classified, step 304 may be implemented to determine a corresponding activity factor. An activity factor may correspond to brisk running, running at a moderate pace, walking slowly or any other activity. An activity factor for an activity may be related to calories or energy generally required to perform the activity. If an activity was not classified in step 302, a default activity factor may be selected or derived. In some embodiments multiple default activity factors may be utilized. An activity's intensity, duration or other characteristic(s) may be assessed, from which one or more default activity factors may be applied. The plural activity factors may be set via medians/averages, ranges, or other statistical approaches.

In various embodiments of the invention, activity factors are used to calculate energy expenditure points. After at least one of user's 124 activity is classified, in step 306 energy expenditure points may be calculated. The use of energy expenditure points allows for comparison of activity levels and may promote collaboration among users, normalize for competition among users of different capabilities, and otherwise encourage activity.

In one embodiment, energy expenditure points are calculated as follows:

$$EEPs = AF * D \quad \text{(equation 1)}$$

wherein EEPs refer to energy expenditure points; AF refers to the activity factor determined in step 304; and D refers to the duration of the activity classified in step 302.

Step 306 may be performed at a device that includes sensors that monitor activity and/or at another device that includes a processor, such as a mobile phone (see, e.g., 138) or server (see, e.g., 134).

In some embodiments equation 1 may be modified to include a scalar that is multiplied by the activity factor and duration. The scalar may be selected so that typical energy expenditure points fall within a desired range. The range of points may be desired for various games or competitions.

Variations of equation 1 may be used in other embodiments of the invention. In some embodiments, users may select an equation and/or one or more variables, such as for example, a scalar. Equations may be selected for different games and competitions. In one example a group may set handicaps among the players based on fitness, so that the most fit generate EEPs only if they do a common activity or set of activities for longer period(s) of time. A group of users participating in an energy expenditure point competition may agree on a particular equation or method before beginning the competition. In some embodiments of the invention, a user may participate in multiple competitions and earn different points for the same activity because of different calculation methods. For example, a user may be participating in two competitions that have unique calculation methods. The user may earn two different point totals for the two different games and a third point total foe their overall energy expenditure. Some point totals may be maintained separate from an overall point total.

After the energy expenditure points are calculated, the calculated points may be combined, such as being added, to a total in step 308. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

Energy expenditure points may be deducted when user 124 has been inactive for a predetermined period of time or enhanced when certain criteria are met. This feature may be included with all calculations or may be used in various games and competitions. For example, in step 314 it may be determined whether an adjustment criteria has been met. The adjustment criteria may include inactivity for a predetermined time period. In some embodiments inactivity is not determined by merely determining that an amount of time has passed since with user was active.

When an adjustment criteria has been met, the total of energy expenditure points may be adjusted in step 310. The adjustment may be a function of duration of inactivity. In some embodiments, a device may warn user 124 (or authorized groups/individuals) that they are close to receiving a reduction in energy expenditure points to encourage activity. It yet other embodiments, an alarm may notify user 124 (and/or other authorized individuals and/or groups) that they have received a reduction of energy expenditure points. In certain embodiments, team-mates and/or competing users may be notified of a reduction (or potential for reduction). In further embodiments, teachers, trainers, and/or parents may more readily monitor the physical activity of others. When a user has not been inactive, the process may end in step 314. Of course, the method shown in FIG. 3 may be repeated at various intervals and allow for tracking points concurrently for different time periods, such as days, weeks and years.

In another aspect, a device 10, such as device 226 may provide a message based on inactivity or non-active periods. If the device senses that the user has been in a non-active (e.g., low activity) state for a predetermined amount of time, an alert message may be delivered to the indicator system or display to remind the user to become more active. The alert message can be delivered in any of the manners described herein. The threshold levels of a low activity state and amount of inactive time could also vary and be individually set by the user.

In some arrangements, user non-activity or inactivity may also be detected and affect the user's progress toward completion of an activity goal. For example, inactivity may be detected when a user does not exhibit movement of a particular level or a type of movement for a specified amount of time, does not exhibit a heart rate of at least a threshold level, does not move a sufficient amount of distance over an amount of time and the like and/or combinations thereof. For arrangements in which a user accumulates activity points to reach an activity point goal, points or a value may be deducted from the user's activity point or other activity metric total when an amount of non-activity (e.g., inactivity or sedentary state) is detected. Various conversion rates for converting inactivity to activity point deductions may be used. In a particular example, 10 minutes of inactivity may correspond to a 5 point deduction. In another example, 30 minutes of inactivity may correspond to a 100 point deduction. Loss or deduction of activity points may be linear or may be non-linear, for example, exponential, parabolic and the like.

A user's non-active time may include inactive time and sedentary time. Inactivity and sedentary time may be defined by different movement, heart-rate, step or other thresholds or may be defined using the same thresholds. In one example, sedentary time may have a higher threshold (e.g., requiring a higher level of activity) than an inactivity threshold. That is, an individual may be considered sedentary but not inactive. The non-active threshold may correspond to the sedentary threshold or a higher threshold, if desired. Alternatively, an inactivity threshold may be greater than a sedentary threshold. There may also be multiple sedentary thresholds, inactivity thresholds and/or non-active thresholds (e.g., each of the sedentary and inactivity thresholds may be a non-active threshold). Different point deductions or rates of point deductions may also be defined between the multiple thresholds and levels of little to no activity (e.g., non-activity). For example, a user may lose 50 points per hour for inactivity and 30 points per hour for sedentary activity or vice versa. Further, activity point deduction may be triggered at different times depending on if the user is inactive or sedentary. For instance, a user may begin losing activity points after 30 minutes of inactivity or 45 minutes of being sedentary. Additional thresholds (e.g., more than two thresholds) and corresponding rates of activity point loss may also be defined.

In some arrangements, various sensors may be used to detect non-active periods of time. As discussed, non-activity time periods may be defined based on heart-rate, amplitude of a movement signal, step rate (e.g., <10 steps per minute), or the like. Alternatively or additionally, inactivity and sedentary time periods may be measured based on a physical position, body position, body orientation, body posture of or type of activity being performed by the individual. The detrimental effects of various physical inactivity or sedentary body positions or orientations may also differ. Accordingly, 30 minutes of reclining may introduce the same health risks as 45 minutes of sitting. The potential for health risks may also be time-dependent. Accordingly, non-activity (e.g., sleeping) for a specified range of durations and during a specified range of time might not introduce health risks. In one example, sleeping for 7-9 hours between 9 PM and 9 AM might not introduce detrimental health risks and thus, might not contribute to activity point or other activity metric value deduction. Indeed, in some example, a lack of inactivity (such as sleep) for a specified range of durations and/or during a specified range of time may be considered detrimental to a user's health. Thus, activity points may be deducted or activity points may be accumulated at a slower rate during these times.

Alternatively or additionally, the amount by which a value of the activity metric (e.g., an activity points) is decreased may be determined based on time of day, location of the user, physical position of the user, level of inactivity and the like. For example, a user may lose greater value in an activity metric and/or at a faster rate during the afternoon than during the evenings. In another example, if a user is at a gym, the user may lose fewer activity points or other activity metric or lose value in the metric at a slower rate than if the user was located at home.

To account for the variances in types of non-active activity (e.g., below a requisite level of movement to be considered activity), a system may distinguish between physical body positions or orientations including, for example, sleeping, reclining, sitting and standing. Distinguishing between different physical body positions and orientations may include placing sensors at different locations of the user's body to detect the individual positions of each body part. The physical body position of the user may then be determined based on the relative positions of the body parts to one another. For example, when a knee location sensor is within a first threshold distance of a waist or chest sensor, the system may determine that the user is sitting. If the knee location sensor is outside of the first threshold distance, the system may determine that the user is standing. In the above example, the system may use a portion of the distance such as the vertical distance. By using vertical distance alone or in combination with an absolute distance (e.g., straight line distance between the two sensors), the system may further distinguish between when a user is lying down and standing up. For example, a lying down position may correspond to a very low vertical distance between the knee sensor and chest or waist sensor even though the absolute distance may be larger. A standing position may correspond to a larger vertical distance between the knee sensor and the waist or chest sensor but exhibit a similar absolute distance. In other examples, an angle formed by the various sensors may be used to determine an individual's position. Additionally or alternatively, the location of the user's various body parts may be evaluated in conjunction with accelerometer or movement data to determine if the user is exhibiting movement or (e.g., at, above or below) a specified level of movement.

In addition to deductions in activity points, the system may alert a user to inactivity to encourage active lifestyles. In one example, the system may alert the user by displaying a message or indicator on a device such as the wearable device assembly described herein after a specified amount of inactivity such as 2 minutes, 5 minutes, 30 minutes, 1 hour and the like. The amount of inactivity time may be additive over non-consecutive time periods. An amount of consecutive inactivity time may alternatively or additionally be tracked. For example, if the user is inactive between 10:15 and 11:00 AM and then again between 2:00 and 2:30 PM, the total amount of non-active time may be 1 hour and 15 minutes. The message or indicator of inactivity may be provided as a warning prior to deducting activity points. For example, the message may indicate that X amount of activity points will be deducted if the user does not exhibit a sufficient level of activity within a specified amount of time (e.g., 30 minutes, 5 minutes, 10 seconds, 30 seconds, 1 hour, 2 hours, etc.). Accordingly, the device may include an non-active timer to determine the amount of user non-activity. Additionally, the message may provide a suggestion as to a type of activity the user should perform to counter any risks introduced by the inactivity. For example, the system may suggest that the user walk 1 hour at a 10 minute mile pace. When the user has counteracted or accounted for the risks or negative effects of the detected amount of inactivity time, a celebratory message or other indication may be provided.

Warnings, point deductions and/or other notifications may be provided if a user returns to a sedentary or a non-active mode within a specified amount of time of exiting sedentary or a non-active mode. For example, the user may exercise or exhibit a sufficient level of activity to exit the sedentary or a non-active mode for a period of 10 minutes. However, the system or device may require at least 30 minutes of activity to avoid additional warnings for a period of time such as 1 hour, 2 hours, 3 hours, etc. For example, the warnings may indicate that the user did not exhibit activity for a sufficient amount of time or a sufficient level of activity or a combination thereof. Additionally, multiple sedentary periods within short amounts of time (e.g., a threshold amount of time) may require higher or additional levels of activity to counteract potential sedentary effects including health risks and the like.

In a particular example, the user may be required to perform a higher level of activity to halt point deduction.

The device or other system may further advise a user as to an amount of non-active time allowed before negative health effects may occur. In one example, the device or system may include a countdown indicating a remaining amount of allowable non-active time before potential health risks may begin taking effect. An amount of permissible non-active time may be earned or accumulated based on an amount of activity performed. Accordingly, the device may also provide suggestions or recommendations as to a type and/or duration of activity that may be performed to earn a specified amount of non-active time (e.g., 1 hour of TV watching). Different types of non-active or sedentary activities may require different types or amounts of activity. For example, 1 hour of reclining may require more strenuous or longer exercise than 1 hour of sitting. In another example, 1 hour of sitting while knitting may require less strenuous or a lower amount of exercise or activity than 1 hour of sitting while watching television. According to one or more arrangements, recommendations may be generated based on empirical data and/or predefined programming and data tables specifying a type and/or duration of activity and a corresponding amount of permissible non-activity.

The device or activity tracking system may further recommend activities based on historical records. For instance, the device or tracking system may determine activity performed by the user in the past and generate recommendations based on those types of activities. Additionally or alternatively, the device or tracking system may generate recommendations for specific workouts performed by the user in the past. For example, a user may need to perform 500 calories worth of activity to counteract 2 hours of TV watching. In such a case, the system may recommend a particular workout performed by the user in the past in which the user burned 500 calories. Combinations of historical activity types and specific historical workouts may be used to generate recommendations. In one example, the system may recommend one of two workouts that the user has performed in the past based on a type of workout that the user appears to prefer. The preference may be determined based on a number of times the user has performed each type of workout. A workout or activity type may also be recommended based on location and time. For example, if a user previously performs a particular type of activity or a particular workout routine at the same location and/or at the same time, the system may recommend that type of activity or workout routine. Other recommendations algorithms and factors may be used.

System 100 may be configured to transmit energy expenditure points to a social networking website. The users may be ranked based on their total number of points for a desired time interval (e.g., rank by day, week, month, year, etc.).

3. SOLDER MASK FOR FLEXIBLE CIRCUIT MEMBER

Figure 5:
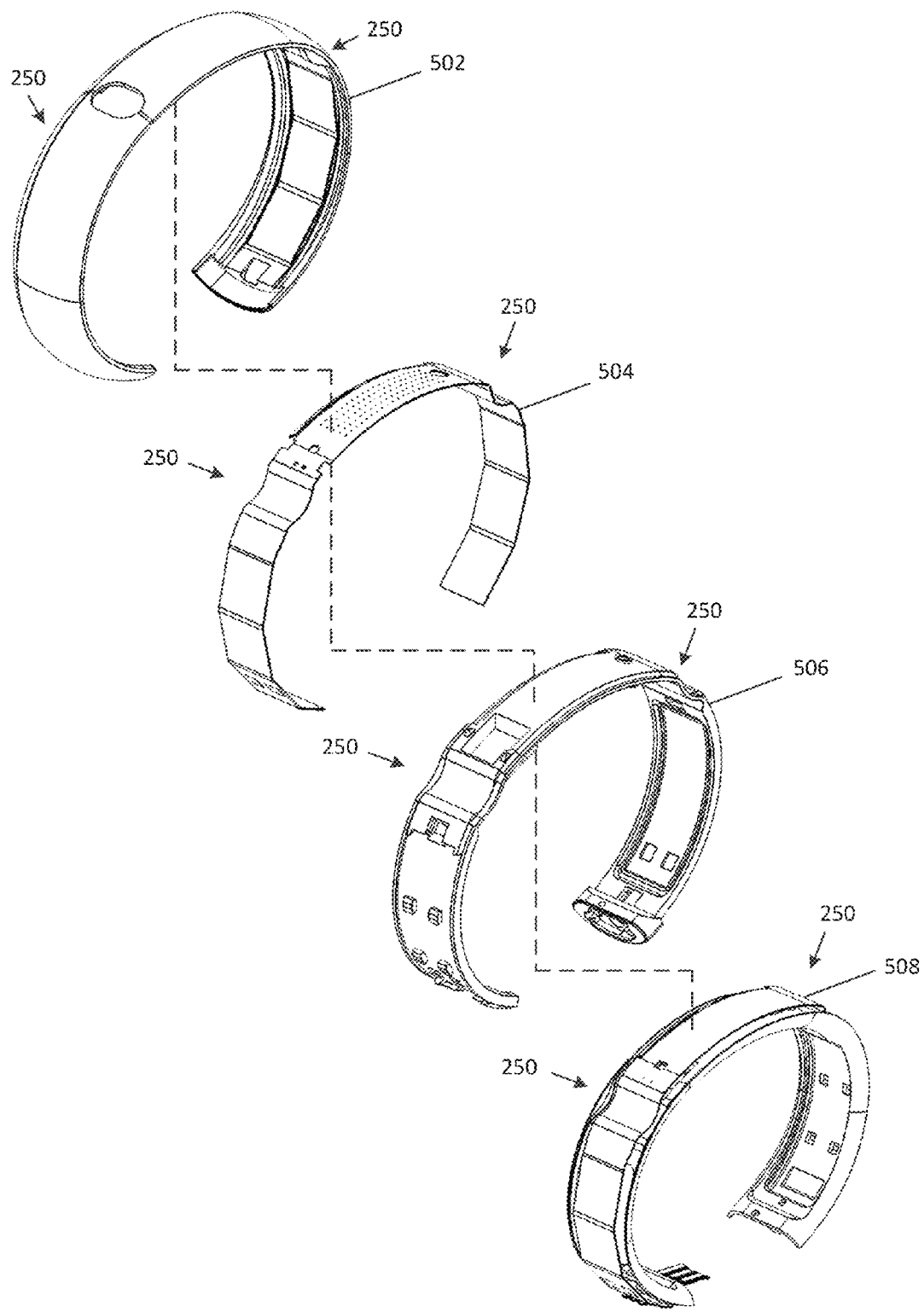
FIG. 5 is an exploded view of portions of the wrist-worn sensor assembly device of FIG. 3.

Referring now to FIG. 5, an exploded view of portions of the wrist-worn device 226 of FIG. 3 is shown. As seen in FIG. 5, example implementations of the wrist-worn device 226 may include an outer over-mold member 502, a flexible circuit member 504, an internal spine member 506, and an inner over-mold member 508. The flexible circuit member 504 may be wrapped around the internal spine member 506. The flexible circuit member 504 and internal spine member 506 assembly may be situated between the outer over-mold member 502 and the inner over-mold member 508. The outer over-mold member 502 and the inner over-mold member 508 may thus form an outer encasement that encloses and protect the flexible circuit member 504 and the internal spine member 506.

As noted above, flex areas 250 of the device 226 permit the device to flex as the device is wrapped around or removed from the wrist of a user. To facilitate the flexing of the device 226, the outer over-mold member 502, the flexible circuit member 504, the internal spine member 506, and the inner over-mold member 508 may also include corresponding flex areas 250 as shown by way of example in FIG. 5. In this example, the flex areas 250 are located near the "shoulders" of the device components. As to the flexible printed circuit member 504, the flex areas 250 comprise deformations. In the example of FIG. 5, flex areas 250 of the member 504 comprise deformations that include a generally concave-shaped surface.

The flexible circuit member 504 may be, for example, a flexible printed circuit board (FPCB or FPC). The flexible circuit member 504, in this example, is wrapped around the internal spine member 506 of the device 226. The flexible circuit member 504 is flexible enough to wrap around the spine member 506. In one example, the flexible circuit member 504 is wrapped toward having the member 504 not only become associated with a substrate (e.g., a spine member 506), but also to conform (e.g., generally, substantially or fully) to the substrate; for example, as shown in FIG. 5, the flexible circuit member 504 is conformally associated with the spine member 506 in device 226. The flexible circuit member 504, so wrapped, may obtain deformations from the substrate, or otherwise, which deformations may arise in one or more locations and/or may have any or varying complexity of contour at each location and among such locations. The flexible circuit member 504 is constructed (including as populated with components) not only so to wrap, but also toward providing robust performance, both mechanically and electronically, in and for the device 226. In the device 226 shown in FIG. 3, for example, the flexible circuit member 504 may be constructed toward surviving both the fabrication of the device 226 and subsequent use (e.g., flexing of member 506 in use of the device 226, such as at either or both flex areas 250). To illustrate the former, the flexible circuit member 504 may be constructed toward surviving the overmold process by which the device 226 is fabricated, which overmold process may induce one or more deformations of the flexible circuit member 504, and which deformations may include: (i) conformities between the flexible circuit member 504 and the spine member 506; (ii) nonconformities between such members 504, 506 (e.g., one or more ripples traversing the width of FPC 504 of device 226, such as adjacent to or otherwise toward the FPC end-directed ends of said device 226, such as, for example in the area, shown in FIG. 6, bounded by USB connectors 607, lines A, B and/or C, and respective lateral sides 614, 616 of flexible circuit member 602). To illustrate the latter, the flexible circuit member 504 may be constructed toward surviving flexing of member 506 in connection with use of the device 226, which flexing may induce one or more deformations (whether plastic or elastic) of the flexible circuit member 504 and which deformations may be (i) at or adjacent either or both flex areas 250 or (ii) otherwise disposed at one or more locations around the periphery of the device 226. Whether deformations of the FPC arise from conforming or nonconforming association with a substrate or other component or structure, or from flexing during use, or from some other mechanism, such deformations impart stress on the FPC 504; as such, robust performance of the FPC may have relationship to, at least in part, the member's construction (e.g., structures and methods) as employed toward surviving any such stress and otherwise toward enhancing the survivability of the FPC 504.

A flexible circuit member 504 may use rolled annealed copper on internal layers (with the grain along the long dimension of the flex), so as to provide superior wear characteristics. In some example implementations, high temperature elongation (HTE) electroformed copper foil—as well as any other types of copper foil that provide more elongation or ductile properties relative to cold rolled copper—may be selectively employed. Some or all of the flex areas 250 of member 504 may have the copper on internal layers, e.g. so as to avoid weakening due to plating (which occurs on external layers) and/or to keep the copper closer to the neutral middle layer. To aid in survivability, one or more, or all junctions in the copper layer where acute or sharp angles would be formed (or otherwise where cracks might arise) may be filleted and rounded out to remove stress concentrations, e.g., toward preventing cracks. Acute or sharp angles of the junctions may represent areas of stress concentrations or stress risers. Examples of these places include junctions between traces and vias, traces and pads, and anywhere where a trace may make a change in direction.

A flexible circuit member 504 may have one or more solder masks. In an example FPC 504, solder masks may be applied to both externally-disposed surfaces, e.g., as to one or more relevant areas of each such surface. As described above, flexing of the wrist-worn device 226 (e.g., repeated flexing thereof) can stress the FPC 504, including by imparting stress to any solder masks applied to the FPC. Some solder masks implementations may experience mechanical failure due to the stress caused by repeated flexing over time, or other deformations. Mechanical failures of the solder mask can lead to mechanical or electrical failures of the FPC 504 and, thus, negatively implicate the FPC survivability. As an example, a solder mask having a substantially straight or linear edge across flex zone 250 may create a stress point for the solder mask, and therefore the solder mask may not be able to sufficiently withstand stress at, adjacent to or otherwise associated with such edge, including, for example, stress from deformations resulting from the flex zone shape and/or the flexing of the wrist-worn device 226 in association with the flex zone 250.

As discussed further below, a solder mask having a nonlinear edge, i.e., a substantially curvilinear edge, may be employed to improve the distribution of stress across the solder mask applied to the FPC 504, e.g., based on deformation of the FPC and/or the solder mask (e.g., during flexing of the wrist-worn device 226). As a result, the survivability of the FPC 504 is advantageously improved. As used in this description, the term "curvilinear" may be additionally or alternatively referred to and understood as curved, nonlinear, and so forth. Furthermore, as used in this description, a curvilinear solder mask edge refers to an edge of a solder mask where at least a portion of the solder mask edge is curved (i.e., arcuate, arched, arced, and so forth). In this regard, example embodiments of the curvilinear solder mask edge may include one or more edge portions that are straight or substantially straight in conjunction with one or more edge portions that are curved.

The design and configuration of the curvilinear solder mask edge may affect how stress is distributed across the solder mask, e.g., during flexing of the wrist-worn device 226. The distribution of stress across the solder mask may depend on various characteristics of the curvilinear solder mask edge including the overall shape of the curvilinear solder mask edge as well as the curvature of various sub-portions of the curvilinear solder mask edge. The example configuration and design for a curvilinear solder mask edge described below distributes the stress across the solder mask, e.g., resulting from repeated flexing of the wrist-worn device 226, thereby improving the survivability of the FPC 504 within the wrist-worn device, e.g., by reducing the likelihood that traces of the FPC 504 will crack or break.

It should be understood that this description of the example curvilinear solder mask edges, edgewith reference to FIGS. 6, 7A-B, and 8, are only examples. Accordingly, some of the features of the example curvilinear solder mask edges described below may not be present in alternative embodiments of curvilinear solder mask edges or may be present in various combinations. None of the features of the example curvilinear solder mask edges described below with reference to FIG. 6, 7A-B, or 8 should be construed to limit the scope of, or the scope of protection for, the designs and configurations of alternative curvilinear solder mask edges.

Figure 6:
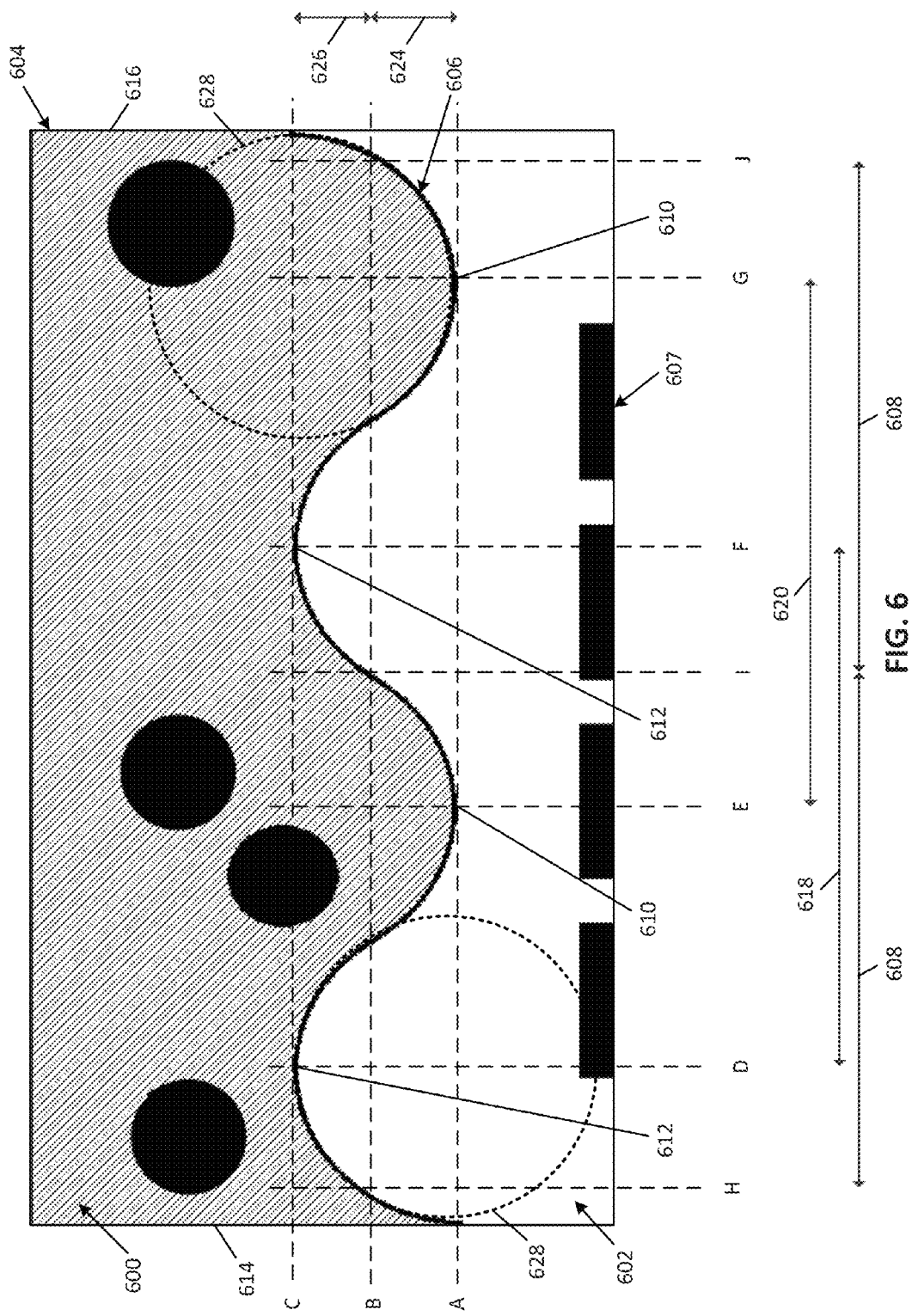
FIG. 6 is an example of an implementation of a solder mask for a flexible circuit member of a wrist-worn device.

Referring to FIG. 6, an example of an implementation of a solder mask 600 for a flexible circuit member 602 of a wrist-worn device 604 is shown. The example solder mask 600 in FIG. 6 is depicted as the hatched or shaded area on the top end of the flexible circuit member 602. The solder mask 600, in this example, includes a curvilinear edge 606 that distributes stress caused by flexing of the flexible circuit member 602 when the wrist-worn device 602 undergoes flexing. The solder mask 600 applied to the flexible circuit member 602 may include one or multiple curvilinear solder mask edges 606. For example, the solder mask 600 may include a curvilinear solder mask edge 606 wherever there is a break in the solder mask, i.e., wherever there is a boundary where the solder mask 600 ends on the flexible circuit member 602. The solder mask 600 may also include a curvilinear solder mask edge near, for example, component contacts or traces on the FPC.

As seen in FIG. 6, the wrist-worn device 604 may include a boundary between the solder mask 600 and the flexible circuit member 602 near the USB connector 607 of the wrist-worn device. Accordingly, the solder mask 600 may include a curvilinear solder mask edge 606 positioned proximate to the USB connector 607 of the wrist-worn device 604. The solder mask 600 may include other curvilinear solder mask edges at additional or alternation locations around the flexible circuit member 602. Alternative embodiments may, for example, include one curvilinear solder mask edge at one end of the solder mask and an additional curvilinear solder mask edge at an opposite end of the solder mask. Furthermore, some example embodiments may include multiple solder masks each including one or more respective curvilinear solder mask edges that distribute stress near components other than the USB connector.

The curvilinear solder mask edge 606 shown by way of example in FIG. 6 may be described as a periodic wave. Various types of periodic waves may be selectively employed for the curvilinear solder mask edge. The example curvilinear solder mask edge 606 in FIG. 6 may be described as a sinusoidal periodic wave, that is, resembling a sine wave. In this regard, the curvilinear solder mask edge 606 may include one or more cycles 608. A cycle 608 of the solder mask edge 606, in this context, refers to a portion of the curvilinear solder mask edge 606 that completes one full oscillation with respect to a reference line, e.g., reference line B in FIG. 6. In one embodiment, a plurality of cycles, such as one or more of cycle 608 of the sinusoidal solder mask edge 606 may generally be understood as a repeating curve pattern of the solder mask edge. Accordingly, the curvilinear solder mask edge 606, in this example, may be described as defining various solder mask peaks 610 ("peaks") and solder mask valleys 612

("valleys") as the curvilinear solder mask edge extends from one lateral side 614 of the flexible circuit member 602 to the other lateral side 616 of the flexible circuit member. Peaks 610 and valleys 612 may also be referred to as crests and troughs respectively. It will also be understood and appreciated that some example embodiments of the curvilinear solder mask edge may include half-cycles (i.e., half-curve patterns, a single arc, etc.) and that a half-cycle may start at any point in the cycle (i.e., curve pattern). Accordingly, with respect to the repeating curve pattern discussed above (i.e., the sinusoidal cycle 608), a half-cycle may be a peak 610, a valley 612, a portion of a peak, or a portion of a valley along the curvilinear solder mask edge 606. Additionally, although a sinusoidal solder mask edge 606 is shown by way of example in FIG. 6, it will be further appreciated that example embodiments of the curvilinear solder mask edge may exhibit: (i) the shown or some other sinusoidal solder mask edge, including combinations of various sinusoids; (ii) alternative curve shapes that repeat one or more curve patterns; (iii) alternative curve shapes that do not repeat a curve pattern; and/or (iv) additional or alternative curve shapes, curve patterns, repetition variations or other characteristics. Additionally, in some example embodiments of the curvilinear solder mask edge, the curves or arcs of the curvilinear edge may avoid forming acute angles or structures, e.g., such that relatively sharp, pointed or abrupt transitions are avoided and relatively gradual transitions are achieved.

A cycle 608 of the curvilinear solder mask edge 606 may include one peak 610 and one valley 612. The example curvilinear solder mask edge 606 of FIG. 6 may be described as having a cycle 608 extending between reference line H and reference line I as well as a cycle extending between reference line I and reference line J. Additional or alternative reference lines may be utilized to describe the cycles of a curvilinear solder mask edge. For example, the curvilinear solder mask edge 606 of FIG. 6 may also be described as having a cycle extending between reference line D and reference line F as well as a cycle extending between reference line E and reference line G. In FIG. 6, the example curvilinear solder mask edge 606 may be described as having two full cycles 608. Some example embodiments of a curvilinear solder mask edge may include from one-half cycle up to eight half-cycles (i.e., up to four cycles). In some example embodiments where the curvilinear solder mask edge resembles a periodic wave, the number of cycles may be based on a ratio of cycles per unit width. In still other embodiments, the curvilinear implementation may include a variety of arcs, curves, lines and other segments, such that the mask edge may be more clearly described by reference to these segments, their numbers, respective arrangement, peaks, valleys, etc., rather than to cycles or half-cycles, but in any case, yet providing distribution of imparted stress, e.g., caused by deformations of the solder mask, including deformation arising via fabrication-based conformities or nonconformities and/or via flexing of the flexible circuit member 602.

As seen in FIG. 6, the example solder mask edge 606 alternates between peaks 610 and valleys 612 as the curvilinear solder mask edge extends between the lateral sides 614 and 616 of the flexible circuit member 602. As noted above, the distribution of stress across the solder mask 600 may depend on various characteristics of the curvilinear solder mask edge 606. With respect to the example curvilinear solder mask edge 606 shown by way of example in FIG. 6, these characteristics may include: the number of peaks 610 and valleys 612 defined by the curvilinear solder mask edge 606; the arrangement of the peaks 610 and valleys 612 along the curvilinear solder mask edge 606; the width 618 of the peaks 610 and the width 620 valleys 612; the height 624 of the peaks 610 and the depth 626 of the valleys 612; and the relation between the width, height, and depth of the peaks and valleys.

In some example implementations, one of the solder mask peaks 610 may be positioned adjacent to one lateral side 616 of the flexible circuit member 602 with one of the solder mask valleys 612 positioned adjacent to the opposite lateral side 614 of the flexible circuit member 602. Additionally, the curvilinear solder mask edge 606, in some example implementations, may define the same total number of peaks 610 as the total number of valleys 612. It will be understood with the benefit of this disclosure that alternative arrangements of peaks 610 and valleys 612 and alternative total numbers of peaks and valleys may be selectively employed. As noted above, the solder mask 600 applied to the flexible circuit member 602 may include multiple curvilinear solder mask edges 606; some or all portions of one or more of these curvilinear solder mask edges may be in phase with respect to one another or may be out of phase with respect to one another, e.g., a peak (or valley) of one edge may be in phase, or out of phase (e.g., including variously out of phase) with a corresponding peak (or valley) of one or more other such edges. As discussed throughout this disclosure, including at least FIG. 8 and paragraphs 83-85 below, solder mask edges (e.g., solder mask edges 606) are not limited to distinct waves having defined frequencies or other attributes that are periodic in nature; accordingly, "in phase" or "out of phase" concepts are understood to apply to various waves formed by solder mask edges forming waves, e.g., as to a peak or a valley of one solder mask disposed on one FPC surface with respect to a corresponding peak or valley of a second solder mask disposed on an opposite FPC surface.

The respective widths 618 and 620 of the peaks 610 and valleys 612 may affect the distribution of stress of the solder mask, e.g., stress caused by flexing of the flexible circuit member 602, or otherwise caused. As seen in FIG. 6, peak width 618 may be described as the distance between the respective minima of the valleys 612 adjacent to the peak 610, e.g., the distance between reference line D and reference line F in FIG. 6. Similarly, valley width 620 may be described as the distance between the respective maxima of the peaks 610 adjacent to a valley 612, e.g., the distance between reference line E and reference line G in FIG. 6.

The width of the wrist-worn device 604 may be approximately around 15.0-20.0 mm (0.59-0.79 in), which width generally establishes a maximum width of a flexible circuit member used within such device 604. Given such example device width and the wave edge shown in FIG. 6, associated examples of peak width 618 or valley width 620 may be approximately around 2-10 mm (0.07-0.40 in). In some example embodiments, peak width 618 and valley width 620 may be approximately around 8 mm (0.31 in). Additionally, in some example implementations, each peak 610 of the curvilinear solder mask edge 606 may exhibit the same peak width 618, i.e., a matching peak width, while in other example implementations the respective peak widths of two or more peaks 610 may be different. Similarly, in some example implementations, each valley 612 of the curvilinear solder mask edge 606 may exhibit a matching valley width 620 while in other example implementations the respective valley widths of two or more valleys 612 may be different. Moreover, in some example implementations, the peak width 618 and the valley width 620 may be the same while in other example implementations the peak width 618 and valley width 620 may be different. It will be understood with the benefit of this disclosure that additional or alternative peak widths 618 and valley widths 620 may be selectively employed.

Similar to peak width 618 and valley width 620, the height 624 of the peaks 610 and the depth 626 of the valleys 612 of the curvilinear solder mask edge 606 may affect the distribution of stress of the solder mask, e.g., stress caused by flexing of the flexible circuit member 602, or otherwise caused. As an example, stress concentrations will be spread across the area of the solder mask 600 between the height 624 of the peaks 610 and the depth 626 of the valleys 612 during flexing of the flexible circuit member 602. The relatively larger area associated with the solder mask 600 in this region (e.g., compared to a straight-edged solder mask) advantageously results in a relatively lower stress force per unit area (FPA). In an illustrative example, FPA may be determined variously, including using numerical techniques (e.g., finite element analysis) or formula (e.g., a formula may provide an approximation) such as FPA=SUM(Force)/(FPA=H×W), where, H=the sum of the distances 624 and 626, W=the width of the flexible circuit member 602 and SUM(Force) represents the forces applied in the area given by H×W. As seen in FIG. 6, peak height 624 may be distance between a reference line and a maximum of the peak 610, e.g., the distance between reference line B and line A. Likewise, valley depth 626 may be the distance between a reference line and a minimum of the valley 612, e.g., the distance between reference line B and line C. Alternative reference lines may be used. As an example, peak height may be the distance between the minimum of a valley 612 and the maximum of a peak 610 immediately adjacent such valley 612; for example, peak height by this measure may be provided by the distance between line C (i.e., associated with the minimum of valley 612) and line A (i.e., associated with the maximum of peak 610). Likewise, valley depth 626 may alternatively be the distance between the maximum of a peak 610 and the minimum of a valley 612 immediately adjacent such peak 610, e.g. the distance between line A and line C.

In the event that the curvilinear solder mask edge 606 may trace or resemble a sine wave in certain embodiments, the sum of the peak height 624 and the valley depth 626 in a cycle (or period) of such wave may be understood as the amplitude of the curvilinear edge of the solder mask. In such or other example embodiments, peak height 624 and valley depth 626 may be proportional to peak width 618 or valley width 620. For example, peak height 624 and valley depth 626 may be approximately around 10-20% (i.e., 1/10-1/5) of the peak width 618 or valley width 620. In some example implementations, peak height 624 and valley depth 626 may be around 12.5% (i.e., 1/8) of the peak width 618 or valley width 620. As such, in some example implementations wherein peak width 618 and/or valley width 620 may be approximately around 2-10 mm (0.07-0.40 in), peak height 624 may be approximately around 0.2-2 mm (0.0079-0.0787 in), and valley depth may 626 be approximately around 0.2-2 mm (0.0079-0.0787 in). In some example implementations, each peak 610 of the curvilinear solder mask edge 606 may exhibit the same peak height 624, i.e., a matching peak height. Similarly, in some example implementations, each valley 612 of the curvilinear solder mask edge 606 may exhibit a matching valley depth 626. In other example embodiments, the peak height 624 of two or more peaks 610 may be different and the valley depth 626 of two or more valleys 612 may be different. Moreover, in some example implementations peak height 624 may match valley depth 626 while in other example embodiments the peak height may be different from the valley depth. It will be understood with the benefit of this disclosure that additional or alternative peak heights and valley depths may be selectively employed.

The shape of the peaks 610 and the shape of the valleys 612 may affect the distribution of stress of the solder mask, e.g., stress caused by flexing of the flexible circuit member 602, or otherwise caused. In the example curvilinear solder mask edge 606 of FIG. 6, the peaks 610 and valleys 612 substantially conform to a portion of a circle 628. Additional or alternative shapes for the peaks 610 and valleys 612 may be respectively employed. For example, individual peaks 610 and valleys 612 of the curvilinear solder mask edge 606 may substantially conform to any portion of a circle, ellipse, parabola, or any other arcuate shape. It will be understood that portions of the curvilinear solder mask edge may be circular, elliptical, parabolic or any other rounded shape.

Figure 7A:
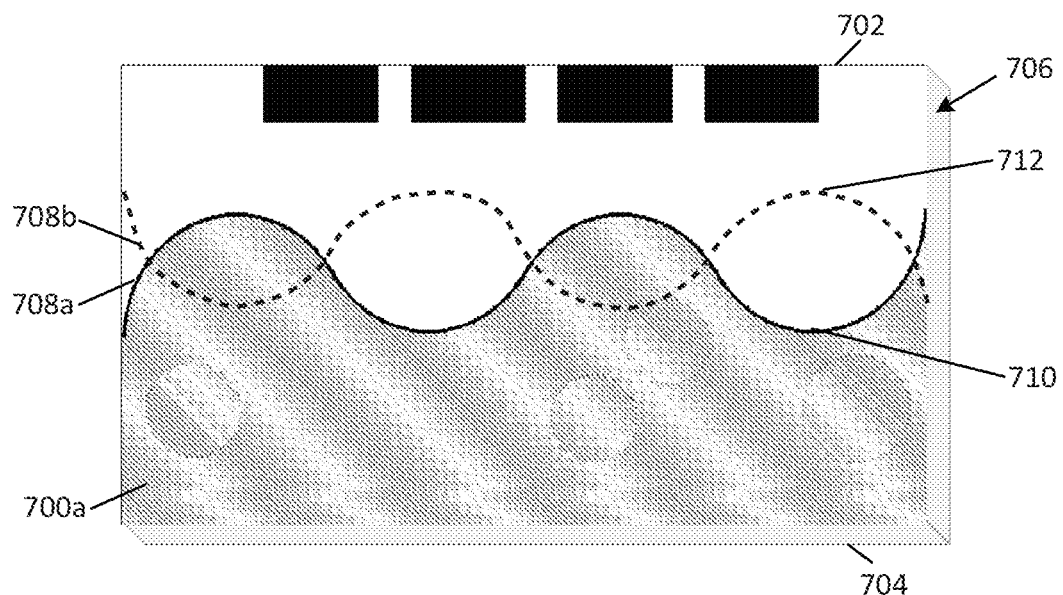
FIG. 7A is an example of an implementation of a first solder mask applied to a first side of a flexible circuit member.
Figure 7B:
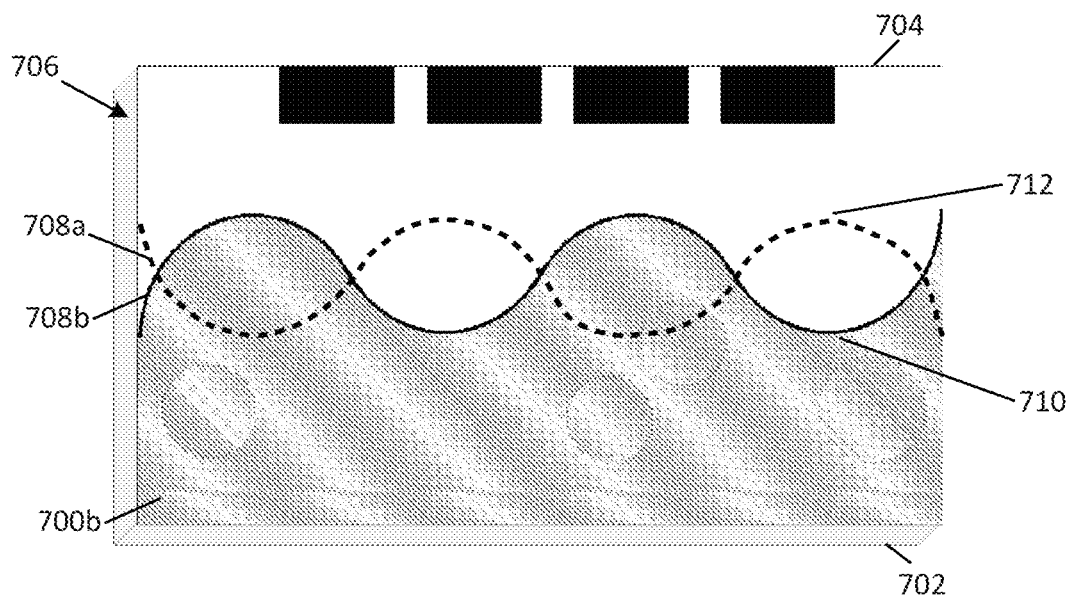
FIG. 7B is an example of an implementation of a second solder mask applied to an opposite side of the flexible circuit member of FIG. 7A.

It will also be understood that respective solder masks may be applied to both the upper surface and the lower surface of a flexible circuit member. Referring to FIGS. 7A-B, example implementations of solder masks 700a and 700b are shown respectively applied to an upper surface 702 and a lower surface 704, adjacent one end of a flexible circuit member 706. As seen in FIG. 7A, the solder mask 700a on the upper surface 702 of the flexible circuit member 706 includes a curvilinear solder mask edge 708a. As seen in FIG. 7B, the solder mask 700b on the lower surface 704 of the flexible circuit member 706 includes a curvilinear solder mask edge 708b. The upper surface 702 of the flexible circuit member 706 may correspond to the surface of the flexible circuit member farthest from and directed away from the wrist of the user when the device is worn around the wrist. The lower surface 704 of the flexible circuit member 706 may correspond to the surface of the flexible circuit member closest to and directed toward the wrist of the user when the device is worn around the wrist of the user.

FIGS. 7A-B illustrate the relative position and arrangement of the solder mask edges 708a and 708b relative to one another. It will be understood that the design, configuration, position, and arrangement of the curvilinear solder mask edges 708a and 708b in FIGS. 7A-B is by way of example only and that additional or alternative designs, configurations, positions, and arrangements may be selectively employed. In FIG. 7A, the solder mask edge 708b on the lower surface 704 of the flexible circuit member 706 is depicted as a dotted line. Similarly, in FIG. 7B, the contour of the solder mask edge 708a on the upper surface 702 of the flexible circuit member 706 is similarly depicted as a dotted line. As seen in FIGS. 7A-B, the example solder mask edges 708a and 708b exhibit a substantially sinusoidal shape similar to the example curvilinear solder mask edge described above. Additionally, the solder mask edges 708a and 708b in FIG. 7A and FIG. 7B are out of phase with one another, i.e., the respective peaks and valleys of the respective solder mask edges are not aligned. It will be understood, however, that example embodiments of curvilinear solder mask edges respectively applied to an upper surface 702 and a lower surface 704 of a flexible circuit member 706 may be in phase with each other or out of phase with each other. Additionally, example embodiments of curvilinear solder mask edges may be out of phase with each other at varying amounts of phase difference. As noted repeatedly above, example embodiments of curvilinear solder mask edges may not resemble periodic waves and thus, the discussion of phases may not be relevant to those example embodiments. In FIGS. 7A-B, the solder mask edges 708a and 708b are out of phase by approximately one half-cycle such that the solder mask edge 708a on the upper surface 702 of the flexible circuit member 706 includes a valley 710 where the corresponding portion of the solder mask edge 708b on the lower surface 704 includes a peak 712. Alternative embodiments of curvilinear solder mask edges respectively applied to an upper surface 702 and a lower surface 704 of a flexible circuit member 706 may, for example, be out of phase by approximately one-quarter cycle, one-eighth cycle, or any other fraction or multiple of a cycle that provides out of phase curvilinear solder mask edges. In some example embodiments, one or more of the peaks of one of the solder masks may align (more or less) with one or more of the peaks of the opposite solder mask; one or more of the valleys of one of the solder masks may align (more or less) with one or more of the valleys of the opposite solder mask; one or more of the valleys of one of the solder masks may align (more or less) with one or more of the peaks of the opposite solder mask; and one or more of the peaks of one solder mask may align (more or less) with one or more of the valleys of the opposite solder mask. In some example embodiments, the peaks or valleys of one of the solder mask may not align with any of the peaks or valleys of the opposite solder mask. As discussed throughout this disclosure, including at least FIG. 8 and paragraphs 83-85 below, solder mask edges (e.g., 708a, 708b) are not limited to distinct waves having defined frequencies or other attributes that are periodic in nature.

Finally, it will be understood that the respective curvilinear solder mask edges respectively applied to the upper surface 702 and the lower surface 704 of the flexible circuit member may exhibit the same curvature or different curvatures. In some example implementations, the flexible circuit member 706 may include electronic components positioned at different locations on the upper surface 702 or the lower surface 704, which the curvilinear solder mask edge may need to curve around or enclose. As a result, the shape of the curvilinear solder mask edge may depend on the placement and arrangement of electronic components. Accordingly, the electronic components of the flexible circuit member 706 may result in non-matching curvilinear solder mask edges on opposed surfaces at an end of the FPC.

Examples of alternative embodiments of the curvilinear solder mask edges may, for example, include solder mask edges where: one of the solder mask edges is sinusoidal while the opposite solder mask edge is not sinusoidal; one of the solder mask edges includes a repeating curve pattern while the opposite solder mask edge does not include a repeating curve pattern; one of the solder mask edges includes one type of curve pattern while the opposite solder mask edge includes a different type of curve pattern; the solder mask edges resemble a periodic wave other than a sinusoidal wave; the solder mask edges exhibit respective curvatures that do not resemble a periodic wave; the solder mask edges have different curvature dimensions (e.g., height, width, depth, slope, etc.); and so forth.

Figure 8:
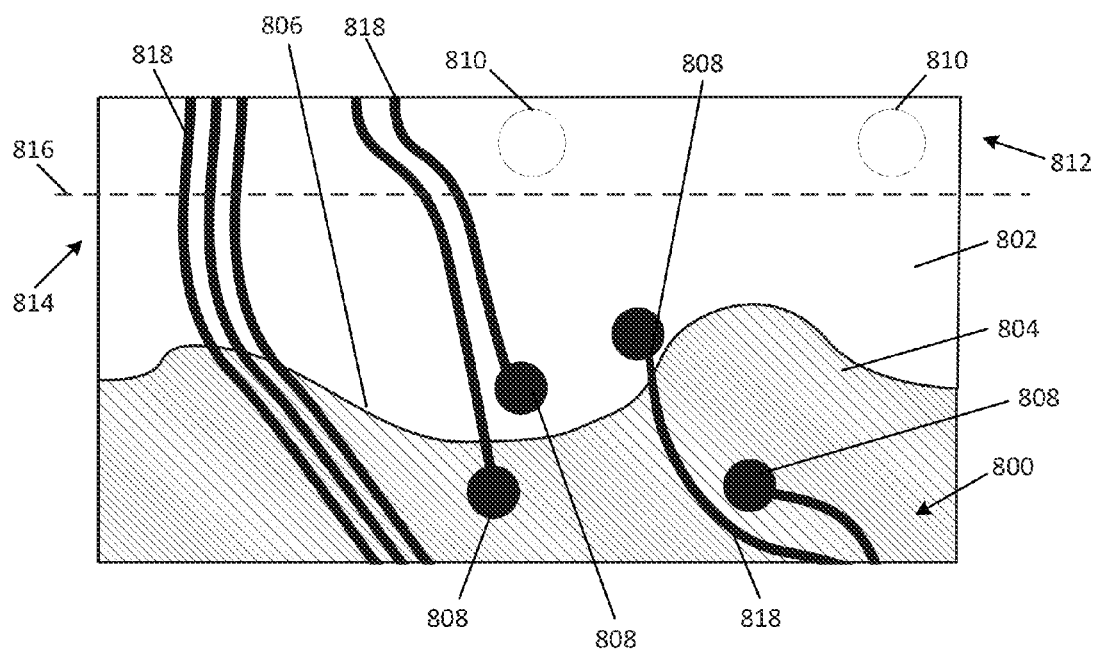
FIG. 8 is another example of an implementation of a curvilinear solder mask edge applied to a flexible circuit member.

FIG. 8 is an example of an implementation of a solder mask 800 applied to a flexible circuit member 802 where the solder mask includes a curvilinear solder mask edge 804 that does not resemble a periodic wave and does not include repeating curve patterns. As seen in FIG. 8, the example curvilinear solder mask edge 804 includes a substantially straight edge portion 806 as discussed above. Additionally, the shape of the curvilinear solder mask edge is configured to curve around various electrical components 808 of the flexible circuit member 804.

FIG. 8 also illustrates construction structures and methods that may be employed, alone or in conjunction with a curvilinear solder mask edge, toward enhancing the survivability of the FPC, including toward enhancing the ability of the FPC to survive stress imparted thereto via any source, including via various deformations (e.g., deformations associated with the flex zones of the FPC and the flexing of the flexible circuit member). As an example, components of the flexible circuit member may be located, positioned, dimensioned, shaped, and so forth, so as to reduce or eliminate the stress either introduced, concentrated, or otherwise that might be associated with the component. In FIG. 8, for example, one or more components 810 on the flexible circuit member 802 (e.g., tooling holes) may be located in a peripheral region 812. Such peripheral region 812 may be variously determined, including, as examples: (i) a region outside any flex area 814 (250 in FIG. 5) of the flexible circuit member; (ii) an area where the FPC is not deformed in the fabrication process, either via conformal association with the substrate or any production aberrations, such as rippling, and/or (iii) an area wherein stress generally is minimal, e.g., adjacent the USB interconnectors of the flexible circuit member. In FIG. 8, the dotted line 816 identifies where the flex area 814 and the region 812 outside the flex area begin and end respectively. In FIG. 8, as another example, one or more components 810 on the flexible circuit member 802 (e.g., traces 818) may be located on a selected (e.g., inner) surface of the FPC, i.e., a surface other than (i) the top or bottom surfaces or (ii) any other surfaces or areas of the FPC wherein traces may be (a) plated or otherwise protected in any manner that may reduce their elasticity and/or (b) associated with a stress concentrator, like a solder mask or ripple. Additionally or alternatively, the traces 818 of the flexible circuit member 802 may exhibit gradual curves so as to avoid stress concentrations on the traces. As seen in FIG. 8, the example traces 818 may be formed so as to curve gradually, e.g., such as across a flexible zone 250 or other FPC deformation, or across an area of stress as to the flexible circuit member 802. Additionally or alternatively, the traces 818 of the flexible circuit member 802 may be routed so as to avoid stress regions, e.g., concentrators, particularly in a stress region wherein stress is accompanied by one or more structures that are stress concentrators. As an example, each trace 818 that electrically couples to a respective one of the USB interconnect pads (such pads shown in FIGS. 6 and 7) may contact that respective pad in an internal portion of that pad (e.g., rather than at peripheral edge of such pad), and therefrom route through a via to an inner surface of the FPC, and therefrom route along the length of, but between, the pads, so as to emerge beyond the transverse edge of the pads (such transverse edge being directed toward the FPC components), so emerging without passing directly under such transverse edge of any pad, and therefrom ultimately to couple with one or more other FPC components. In so routing such USB-coupled traces to, the traces avoid passing under the pad's transverse edge, these traces and, as such, avoid this stress concentrator. In an example, so routing such USB-coupled traces avoids the action of the pad edge as a stress concentrator, where stress may be variously imparted, e.g., via an FPC ripple formed adjacent to the USB contacts. One or more of these and other features may be used in combination with the curvilinear solder mask edge, e.g., particularly if sources of stress, e.g., deformations are or may become present.

4. BALL GRID ARRAY

In another aspect of the design, the Ball Grid Array packaged ICs are under-filled. In the over-molding, since the over-mold material might get under such ICs, so as to, e.g., weaken, damage or otherwise make infirm the junction of the IC and the FPC, or even outright cause the IC to come off the FPC. The under-fill step is implemented toward preventing the over-mold material from so getting under the IC. In one embodiment, epoxy is placed (e.g., squeezed out) underneath the BGA packaged IC, so as to fill the void between IC and FPC, substantially fill the void between IC and FPC, or otherwise provide a barrier sufficient to overcome the undesirable implication of the over-molding.

These features can be combined with the several other features described herein as desired.

5. CONCLUSION

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A wrist-worn device that monitors movements of a user comprising:
    a curvilinear body having a plurality of flex areas;
    an internal spine member extending through the body;
    a flexible circuit member wrapped around and connected to the spine member, the flexible circuit member interconnects a controller and one or more sensors of a sensor assembly within the body;
    a solder mask applied to the flexible circuit member wherein the solder mask includes a curvilinear edge such that the curvilinear edge of the solder mask distributes stress caused by flexing of the flexible circuit member; and
    wherein the curvilinear edge of the solder mask defines a plurality of solder mask peaks and a plurality of solder mask valleys between a first side and a second side of the flexible circuit member.

2. The wrist-worn device of claim 1 wherein a total number of solder mask peaks defined by the curvilinear edge of the solder mask equals a total number of solder mask valleys defined by the curvilinear edge of the solder mask.

3. The wrist-worn device of claim 1 wherein one of the solder mask peaks of the plurality of solder mask peaks is positioned adjacent to the first side of the flexible circuit member and one of the solder mask valleys of the plurality of solder mask valleys is positioned adjacent to the second side of the flexible circuit member.

4. The wrist-worn device of claim 1 wherein each solder mask peak of the plurality of solder mask peaks have a matching height.

5. The wrist-worn device of claim 4 wherein the matching height is approximately 1-3 mm.

6. The wrist-worn device of claim 1 wherein each solder mask valley of the plurality of solder mask valleys have a matching valley depth.

7. The wrist-worn device of claim 6 wherein the matching valley depth is approximately 1-3 mm.

8. The wrist-worn device of claim 1 wherein a height of at least one of the solder mask peaks of the plurality of solder mask peaks matches a valley depth of at least one of the solder mask valleys of the plurality of solder mask valleys.

9. The wrist-worn device of claim 1 wherein a shape of at least one of the solder mask peaks of the plurality of solder mask peaks substantially conforms to a portion of a circle.

10. The wrist-worn device of claim 1 wherein a shape of at least one of the solder mask valleys of the plurality of solder mask valleys substantially conforms to a portion of a circle.

11. The wrist-worn device of claim 1 wherein each solder mask peak of the plurality of solder mask peaks have a matching peak width.

12. The wrist-worn device of claim 11 wherein the matching peak width is approximately 2-10 mm.

13. The wrist-worn device of claim 1 wherein each solder mask valley of the plurality of solder mask valleys have a matching valley width.

14. The wrist-worn device of claim 13 wherein the matching valley width is approximately 2-10 mm.

15. The wrist-worn device of claim 1 wherein the solder mask is a first solder mask of the wrist-worn device and is applied to a first surface of the flexible circuit member and further comprising:
    a second solder mask applied to a second surface of the flexible circuit member, the second surface disposed opposite the first surface; and
    wherein the second solder mask includes a second curvilinear edge such that the second curvilinear edge of the second solder mask distributes stress caused by flexing of the flexible circuit member.

16. A solder mask of a flexible circuit member of a wrist-worn device that monitors movements of a user, the solder mask comprising:
    a curvilinear edge positioned proximate to a USB connector of the wrist-worn device such that the curvilinear edge of the solder mask distributes stress caused by flexing of the flexible circuit member;
    wherein the curvilinear edge defines a plurality of solder mask peaks and a plurality of solder mask valleys between a first side and a second side of the flexible circuit member;
    wherein a total number of solder mask peaks defined by the curvilinear edge equals a total number of solder mask valleys defined by the curvilinear edge;
    wherein each solder mask peak of the plurality of solder mask peaks have a matching height; and
    wherein each solder mask valley of the plurality of solder mask valleys have a matching depth.

17. The solder mask of claim 16 wherein:
    each solder mask peak of the plurality of solder mask peaks have a matching peak width; and
    each solder mask valley of the plurality of solder mask valleys have a matching valley width.

18. The solder mask of claim 17 wherein:
    a respective shape of each solder mask peak of the plurality of solder mask peaks substantially conforms to a portion of a circle; and
    a respective shape of each solder mask valley of the plurality of solder mask valleys substantially conforms to a portion of a circle.

19. The solder mask of claim 18 wherein:
    the height of the plurality of solder mask peaks matches the depth of the plurality of solder mask valleys; and the peak width of the plurality of solder mask peaks matches the valley width of the plurality of solder mask valleys.

\* \* \* \* \*